United States Patent
McDaniel et al.

(10) Patent No.: US 8,043,858 B2
(45) Date of Patent: Oct. 25, 2011

(54) DYNAMIC DESALTER SIMULATOR

(75) Inventors: Cato R. McDaniel, The Woodlands, TX (US); Harold J. Eggert, The Woodlands, TX (US); Kevin S. Solomon, Millstone Township, NJ (US); Earl E. Siders, The Woodlands, TX (US); Frank Denison, Richmond, TX (US); Alan E. Goliaszewski, Hockessin, DE (US); David B. Engel, The Woodlands, TX (US); Sherif Eldin, Bellaire, TX (US); Thomas K. Brow, Houston, TX (US)

(73) Assignee: General Electric Company, Schenectady, NY (US)

( * ) Notice: Subject to any disclaimer, the term of this patent is extended or adjusted under 35 U.S.C. 154(b) by 350 days.

(21) Appl. No.: 12/218,456

(22) Filed: Jul. 15, 2008

(65) Prior Publication Data
US 2010/0015720 A1    Jan. 21, 2010

(51) Int. Cl.
*G01N 33/26* (2006.01)
*G01N 21/00* (2006.01)
*G01N 21/01* (2006.01)

(52) U.S. Cl. .......... 436/60; 436/164; 436/174; 436/175; 436/177; 436/40; 422/68.1; 422/82.05; 422/527; 210/708; 208/188

(58) Field of Classification Search .................... 436/40, 436/60, 139, 164, 174, 175, 177; 422/62, 422/68.1, 82.05, 101, 527; 210/708, 723; 208/188, 251 R
See application file for complete search history.

(56) References Cited

U.S. PATENT DOCUMENTS

| | | | |
|---|---|---|---|
| 5,256,305 A * | 10/1993 | Hart | 210/708 |
| 6,113,765 A | 9/2000 | Wagner et al. | |
| 6,228,239 B1 * | 5/2001 | Manalastas et al. | 204/567 |
| 7,008,536 B2 | 3/2006 | Varadaraj et al. | |
| 7,244,364 B1 * | 7/2007 | Weber | 210/729 |
| 2008/0149486 A1 * | 6/2008 | Greaney et al. | 204/570 |

FOREIGN PATENT DOCUMENTS
WO    W02008082512 A2    7/2008

* cited by examiner

*Primary Examiner* — Maureen M Wallenhorst
(74) *Attorney, Agent, or Firm* — Wegman, Hessler & Vanderburg

(57) ABSTRACT

A small-scale dynamic simulator for crude oil refinery desalters has a pressurized oil deviblis configured to hold a supply of crude oil and a water deviblis configured to hold a supply of wash water. At least one chemical feed pump selectively adds emulsion breaker chemicals to the desalter simulator and a low shear metering pump is configured to pump crude oil and wash water through the desalter simulator. An emulsion forming device forms a crude oil-wash water emulsion that is then received in a desalter vessel. The desalting vessel is fitted with electric grids which simulate those found in electric desalters. The emulsion is resolved within the desalter vessel with the assistance of the emulsion breaker chemicals so the wash water and crude oil form distinct phases, with substantially desalted crude oil removed from an upper portion of the desalter vessel and substantially oil-free wash water removed from a bottom portion of the desalter vessel. A portion of the desalter vessel is substantially transparent to allow visualization of the demulsification process and at least one light source is positioned adjacent to the desalter vessel to aid in visualization of a rag layer formed in the desalter vessel. A heated jacket surrounds the desalter vessel to maintain the desalter vessel at the desired temperature.

20 Claims, 1 Drawing Sheet

DYNAMIC DESALTER SIMULATOR

BACKGROUND OF THE INVENTION

1. Field of the Invention

The present invention relates generally to the small-scale simulation of crude oil refinery desalters, free water knockouts and heater treaters, and more particularly, to a dynamic desalter simulator that enables the direct observation of the rag layer at the crude oil and water interface and the ability to remove samples of the fluids or emulsions during the simulation and monitor parameters such as temperature, pressure, conductivity, chloride, and pH.

2. Description of Related Art

Liquid hydrocarbon phase, such as crude oil, naturally contains a variety of contaminants that have detrimental effects on process equipment and in the operation of a refinery. These contaminants are broadly classified as salts, bottom sediment, water, solids, and metals. The types and amounts of these contaminants vary depending on the particular hydrocarbon phase. Additionally, native water present in the liquid hydrocarbon phase as droplets may be coated with naturally occurring surfactants such as asphaltenes, naphthenic acid salts, resins, or with solids including but not limited to iron oxide, silica, carbon, carbonates, or phosphates. Removing the water from the crude oil is essential at crude oil production facilities as it impacts the value of crude oil and its economic transportation. The presence of salts, especially chlorides of Group I and Group II elements of The Periodic Table of Elements, causes corrosion of oil processing equipment. In order to mitigate the effects of corrosion, it is advantageous to reduce the salt concentration to the range of 1 to 5 ppm or less and water content to about 0.10 to 1 wt % by weight of the crude oil prior to transportation and processing of the oil.

A standard treatment for removing small particles of solids and bottom sediment, salts, water and metals is a phase separation operation commonly known as dewatering or desalting. A fresh water wash in the range of typically 4 to 15 vol % is injected into the crude oil. The crude oil and wash water are subjected to shear to thoroughly mix the water and the crude oil to form an emulsion and to transfer the contaminants from the crude oil into the fresh water. Frequently a chemical emulsion breaker is also added to the emulsion, and often the emulsion is subjected to an electrostatic field so that water droplets in the mixture of crude oil, wash water, and chemical emulsion breaker coalesce in the electrostatic field between electrodes. The coalesced water droplets settle below the oleaginous crude oil phase and are removed. The treated crude oil is removed from the upper part of the separator.

One problem encountered with dewatering and desalting is that some crude oils form an undesirable "rag" layer comprising a stable oil-water emulsion and solids at the water-oil phase boundary in the desalter vessel. The rag layer often remains in the vessel but it may be removed for storage or for further processing. Rag layers at the water-oil phase boundary result in oil loss and reduced processing capacity. Heavy crude oils containing high concentrations of asphaltenes, resins, waxes, and napthenic acids exhibit a high propensity to form rag layers.

Additives may be added to improve coalescence and dehydration of the hydrocarbon phase, provide faster water separation, improve salt or solids extraction, and generate oil-free effluent water. These additives, also known as demulsifiers, are usually fed to the hydrocarbon phase to modify the oil/water interface. It is also possible to feed these materials to the wash water or to both the oil and water. These additives allow droplets of water to coalesce more readily and for the surfaces of solids to be water-wetted. The additives reduce the effective time required for good separation of oil, solids, and water.

Development of new chemical demulsifiers has typically been done using static simulations. In the past, static tests using a simple apparatus such as glass bottles or glass tubes and are referred to as "bottle testing". These methods have proven to be useful but they often fail to adequately simulate many critical parameters of a desalter and have been of limited use particularly in heavy oils or systems that have a propensity to develop rag layers. In particular, bottle testing fails to simulate the development of a rag layers since these develop over time in dynamic systems that continually refresh the oil.

In the simplest embodiment, oil samples with treatments are added to prescription bottles and shaken. The rate of demulsification (water removal) is then monitored as a function of time by observing the amount of "free" water that collects at the bottom of the bottle. This simulation is sufficient for desalting vessels that are operated at low temperatures with light oils. However, it fails to correctly simulate the size of the water drops in the actual emulsion and the actual temperature. The equation below is Stokes Law and describes the settling velocity of spherical water drops in a fluid.

$$V_s = \frac{2}{9} \frac{r^2 g (\rho_p - \rho_f)}{\eta}$$

where:
$V_S$ is the particles' settling velocity (cm/sec) (vertically downwards if $\rho_p > \rho_f$, upwards if $\rho_p < \rho_f$),
r is the Stokes Radius of the particle (cm),
g is the gravitation constant (cm/sec$^2$),
$\rho_p$ is the density of the particles (g/cm$^3$),
$\rho_f$ is the density of the fluid (g/cm$^3$), and
$\eta$ is the fluid viscosity (dyne sec/cm$^2$).

The simplistic bottle shaking simulations often fail to correctly simulate the drop diameter and the temperature and viscosity ($\eta$), which is a function of temperature. This results in data that fails to properly describe the system being studied. For heavier oils, the bottle shaking simulation is even worse. Actual desalting temperatures are between 120° C. to 150° C., and these simple simulations are not close to actual conditions of viscosity, drop size and in materials like SAGD fluid or Venezuelan Extra Heavy crude since the density difference between the water and the oil is significant at the higher temperatures. Thus, this driving force for separation is incorrectly simulated. Historically, people add diluents, a light aliphatic hydrocarbon, in efforts to better simulate the viscosity and density differences, but this changes the polarity of the oil and can precipitate the asphaltenes and completely change the nature of the oil. Without the addition of the diluents to reduce the viscosity, the separation time at low temperatures can be many hours.

Dynamic test simulators that allow actual operating conditions of a desalter to be used in the experiments have been built. These devices include "pilot" units that use hundreds of barrels per day to laboratory systems that use 50 to 100 gallons of oil per day. These devices still use sizeable quantities of crude oil, have limited abilities to modify system parameters, and the ability to observe the development of a rag is not possible.

It is desired to improve simulation methods such that one may select the most efficacious chemistries and operating conditions to optimize the emulsion breaker chemistries, oil mixtures, temperatures, emulsion size, and other parameters.

SUMMARY OF THE INVENTION

In one aspect, the invention is directed to a small-scale dynamic simulator for crude oil refinery desalters has a pressurized oil deviblis configured to hold a supply of crude oil and a water deviblis configured to hold a supply of wash water. At least one chemical feed pump selectively adds emulsion breaker chemicals to the desalter simulator, and a low shear metering pump is configured to pump crude oil and wash water through the desalter simulator. An emulsion forming device forms a crude oil-wash water emulsion that is then received in a desalter vessel. The emulsion is resolved within the desalter vessel with the assistance of the emulsion breaker chemicals such that the wash water and crude oil form distinct phases, with substantially desalted crude oil removed from an upper portion of the desalter vessel and substantially oil-free wash water removed from a bottom portion of the desalter vessel. A portion of the desalter vessel is substantially transparent to allow visualization of the demulsification process and at least one light source is positioned adjacent to the desalter vessel to aid in visualization of a rag layer formed in the desalter vessel. A heated jacket surrounds the desalter vessel.

The invention is also directed to a method of testing emulsion breaker chemicals in a dynamic desalter simulator. The method includes the steps of drawing crude oil from a heated and pressurized oil deviblis configured to hold a supply of crude oil and drawing wash water from a water deviblis configured to hold a supply of wash water. At least one emulsion breaker chemical is added to the desalter simulator. The crude oil and wash water are pumped through the desalter simulator with a low shear metering pump and crude oil-wash water emulsion is formed with an emulsion forming device. The method also includes resolving the crude oil-wash water emulsion in a desalter vessel so the wash water and crude oil form distinct phases, with substantially desalted crude oil removed from an upper portion of the desalter vessel and substantially oil-free wash water removed from a bottom portion of the desalter vessel and passing light from a light source through a transparent portion of the desalter vessel to monitor the presence of a rag layer at the interface between the crude oil phase and wash water phase using a light source. Parameters of the dynamic desalter simulator are then adjusted and the effect that the adjustment has upon the rag layer is monitored to find the most efficacious chemistries and operating conditions. The parameters adjusted can include the rate of addition of emulsion breaker chemicals, the type of emulsion breaker chemicals added, the temperature of the desalter vessel, the residence time of crude oil in the desalter vessel, the residence time of wash water in the desalter vessel, and the emulsion size.

The present invention and its advantages over the prior art will become apparent upon reading the following detailed description and the appended claims with reference to the accompanying drawings.

BRIEF DESCRIPTION OF THE DRAWINGS

The above mentioned and other features of this invention will become more apparent and the invention itself will be better understood by reference to the following description of embodiments of the invention taken in conjunction with the accompanying drawings, wherein.

Corresponding reference characters indicate corresponding parts throughout the views of the drawings.

DETAILED DESCRIPTION OF THE INVENTION

Figure 1:
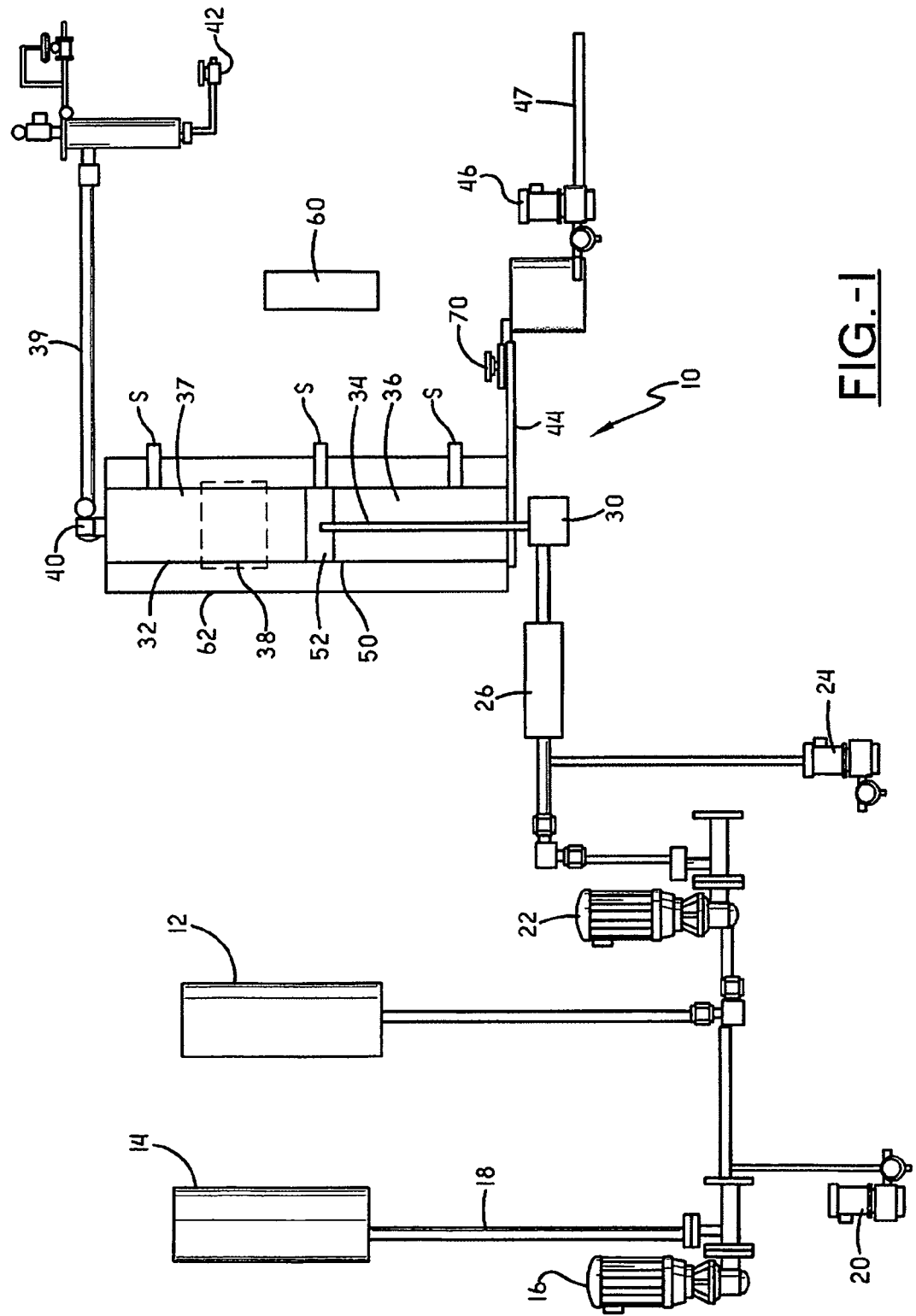
FIG. 1 illustrates a schematic drawing of dynamic desalter simulator.

The invention will now be described in the following detailed description with reference to the drawings, wherein preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications, and equivalents as will become apparent from consideration of the following detailed description.

Referring now to FIG. 1, a desalter simulator 10 is shown that provides the ability to produce operating conditions of a desalter and directly observe the rag layer formed at the oil-water interface as it develops. Additionally, the desalter simulator 10 permits one to observe the development of a rag layer that increases with time and resolves upon the addition of chemical treatment. Testing for the most efficacious chemistries and operating conditions to optimize the emulsion breaker chemistries, oil mixtures, temperatures, emulsion size, and other parameters can be performed using the desalter simulator 10 processing about 4-20 liters of crude oil in an eight hour period. The use of such small amounts of oil to perform the experiments reduces the cost of oil transport and disposal.

The desalter simulator 10 has a pressurized oil deviblis or pressure pot 12 which acts as a source of untreated crude oil. The oil deviblis 12 is desirably a vessel made of steel or stainless steel and has a volume between about 6 to 10 gallons. In one embodiment, the crude oil is contained within an internal can placed within the oil devilblis 12 having a volume of about 5 gallons such that the oil only comes in contact with the internal can so as to minimize the amount of cleanup required or cross contamination. The crude oil within the oil deviblis 12 is stirred with a low shear stirrer and is heated to a temperature of about 100° C. and is pressurized to keep the native water in the crude oil from vaporizing at this temperature. The heated and stirred oil source keeps the feed constant in terms of native water content and solids which could settle during the course of the experiment. Use of a pressurized, heated, and stirred oil deviblis 12 allows heavy oils and extra heavy oils including oils sands derived bitumen to be tested.

The desalter simulator 10 also contains a water deviblis 14. The water deviblis 14 is desirably a vessel made of steel or stainless steel and has a volume of between about 1 and 6 gallons. This water deviblis may contain an internal can of wash water such that it has a similar design to the oil deviblis 12. The wash water may contain hydrogen sulphide or low molecular weight amines. The water deviblis 14 keeps the water in an enclosed container to prevent the loss of these materials and keeps any solids in suspension.

A metering pump 16 located in a wash water addition line 18 pumps water from the water deviblis 14. The metering pump 16 is desirably a progressive cavity pump.

At least one chemical feed pump 20 may selectively add reverse emulsion breaker chemicals to the wash water addition line 18. Desirably, the feed pumps 20 pump at a low dose rate so as to add chemicals in the nL/minute and μL/minute range. Use of multiple chemical feed pumps 20 allows the composition of the product to be varied and studied.

A metering pump 22 pumps oil from the oil deviblis 12 and water from the water deviblis 14. The pump 22 is desirably a low shear pump capable of pumping the crude oil and water without out forming the emulsion. In one embodiment, the metering pump 22 is a progressive cavity pump capable of pumping viscous fluids and slurries. Desirable oil flow rates are between about 2 and 4 liters/hour.

At least one chemical feed pump 24 selectively adds primary emulsion breaker chemicals, which are characteristically surfactants, to the desalter vessel 32 input line. Desirably, the feed pumps 24 are low dose rate so as to add chemicals in the nL/min and uL/minute range. Use of multiple chemical feed pumps 24 allows the composition of the product to be varied and studied.

The crude oil, wash water and emulsion breakers next pass through a static mixer 26. A preliminary mixture is formed when the oil and wash water are brought into contact with each other due to turbulent flow caused by the static mixer 26. The static mixer 26 can be any torturous flow path device known in the art. Next, an emulsion forming device 30 mixes the crude oil and wash water to form an emulsion. In one embodiment, the emulsion forming device 30 is an electrically variable stirring device rather than conventional mix valves which tend to clog and fail at the required small feed rates. The operator can select the velocity or stirring rate of the emulsion forming device 30 to vary the tightness of the emulsion.

The crude-water emulsion from the emulsion forming device 30 continuously enters a desalter vessel 32 through an input line 34 which serves to distribute the incoming emulsion more or less evenly over the cross-section of the desalter vessel 32. The height of the input point of the line 34 in the desalter vessel 32 can be varied to simulate the configurations of the different desalters to be simulated (e.g., bielectric, low velocity, etc.). The desalter vessel 32 permits the operator to simulate useful parameters including but not limited to: desalter vessel temperatures, residence time, electric fields, and vertical velocity. The emulsion is resolved in the desalter vessel 32 with the assistance of the emulsion breaking chemicals and may also be assisted by the known method of providing an electrical field to polarize the water droplets. Once the emulsion is broken, the water and petroleum media form distinct phases. A water phase 36 is separated from a petroleum phase 37 and subsequently removed from the desalter vessel 32. Desirably, the desalter vessel 32 contains a number of sample points S along the height of the vessel 32 so that samples can be taken from various points in the vessel.

In one embodiment, an electric grid 38 is positioned adjacent the desalter vessel 32. The electric grid generates an electrostatic field at potentials ranging from about 6,000 volts to about 10,000 volts to induce dipole attractive forces between neighboring droplets which causes them to migrate towards each other and coalesce. The electrostatic field causes each droplet to have a positive charge on one side and a negative charge on the other. The droplets coalesce because of the attractive force generated by the opposite charges on neighboring droplets. The attractive force is strongly affected by the distance between the droplets and is much stronger when the droplets are in close proximity.

The crude oil residence time in the desalter vessel 32 is desirably between about 15 and 30 minutes. This corresponds to typical residence times for desalters treating crude oil with API gravities from 15 to 28. Residence time in the desalter vessel 32 can be adjusted to test different conditions by adjusting the crude oil flow rate with the metering pump 22. The crude oil rise rate is desirably about 0.15 cm/sec. (0.05 inch/sec.). To provide the desired resident times at this rise rate, the desalter vessel 32 has a height of between about 150 and 190 cm, and in one embodiment is 170 cm (70 inches). The desalted oil 37 flows continuously out of the desalter vessel 32 through a desalted crude oil outlet line 39 via a collector manifold 40. The outlet line 39 leads to a suitable drain 42 for collecting the crude oil. The drain 42 also can be used as a sample point for testing the desalted crude oil.

The larger coalesced droplets settle by gravity into the water phase 36 at the bottom of the desalter vessel 32, and this brine or wastewater can be removed continuously from the bottom via a water discharge line 44. Desirably, the water residence time is between about 60 and about 120 minutes. Wash water residence time in the desalter vessel 32 can be adjusted to test different conditions by adjusting the wash water flow rate with metering pump 14. The water discharge line 44 contains a water metering pump 46 to control the rate of removal of the water and a drain 47. The drain 47 also can be used as a sample point for testing the wash water removed from the desalter vessel 32.

According to the invention, the desalter vessel 32 incorporates substantially transparent tubes 50 to allow visualization of the demulsification process and formation of a rag layer 52 at the crude oil-wash water interface. Desirably, the desalter vessel 32 is made of glass tubes, but other substantially transparent materials may be used. One or more light sources 60 adjacent to the desalter vessel 32 are used to aid in observation of the rag layer 52 formed in the desalter vessel 32. The light sources 60 produce light in the visible light, near IR, and/or UV spectrums and can be of any design known to those skilled in the art. Thus, the transparent desalter vessel 32 allows observation of the demulsification process using not only the visible light spectrum, but also the IR and near IR light spectrums. The transparent desalter vessel 32 permits observation of the effects that changing emulsion breaker chemistries, operating conditions, oil mixtures, temperatures, emulsion size, and other parameters have upon the rag layer. Additionally, analysis of the most efficacious chemistries and operating conditions can be performed using microscopy through the desalter vessel 32 to visualize the emulsion and solids with visible light, near IR, UV, using phase contrast microscopy to visualize the flowing emulsion, and using phase contrast near IR microscopy to visualize the flowing emulsions.

The desalter simulator 10 desirably contains a heated jacket 62 surrounding the desalter vessel 32. Desirably, the heated jacket 62 is an annular jacket using a hot gas or liquid to heat the desalter vessel 32. In one embodiment, hot air is used. Use of the hot air jacket 62 with adjustable temperature and flow is used to maintain the temperature of the desalter vessel 32. Desirably, the hot air jacket 62 maintains the temperature in the desalter vessel 32 between about 150 and 200° C.

In one embodiment, the desalter simulator 10 contains a multiple desalter vessels 32 arranged in parallel channels. Each channel can contain its own chemistry feed pumps 20, 24 to facilitate comparisons of different treatments. Therefore, testing on a specific crude oil composition can be conducted using several different emulsion breaker chemistries, concentrations, and conditions to see which combination provides the most effective treatment. Use of multiple chemical feed pumps 20, 24 allows simulation of "normal' and "split feed" dosing and the optimization of the chemical feed.

The desalter simulator 10 desirably contains at least one device 70 to monitor the concentrations of the salt in the water discharge line. These devices may be chloride electrode, conductivity meters, or other devices known to those skilled in the art. Turbidity meters to monitor the oil levels in the water discharge line are also desirably used. Thus, the desalter simulator provides the ability to remove samples of the fluids or emulsions during the simulation and monitor parameters such as conductivity, chloride and pH, in addition to temperature and pressure.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A dynamic desalter simulator for testing a demulsification process comprising:
    a pressurized oil vessel configured to hold a supply of crude oil;
    a water vessel configured to hold a supply of wash water;
    at least one chemical feed pump to selectively add emulsion breaker chemicals to the crude oil and/or wash water in the desalter simulator;
    a pump configured to pump crude oil from the oil vessel and wash water from the water vessel through the desalter simulator;
    an emulsion forming device configured to form a crude oil-wash water emulsion from the crude oil and wash water pumped through the pump;
    a desalter vessel configured to receive the crude oil-wash water emulsion from the emulsion forming device through an emulsion input line fluidically connected to the emulsion forming device, the height of an input point of said emulsion input line into the desalter vessel being variable with respect to the desalter vessel, wherein the crude oil-wash water emulsion is resolved within the desalter vessel with the assistance of the emulsion breaker chemicals so the wash water and crude oil form distinct phases, with substantially desalted and dewatered crude oil removed from an upper portion of the desalter vessel and substantially oil-free wash water removed from a bottom portion of the desalter vessel, wherein a portion of the desalter vessel is substantially transparent such that the wash water phase and the crude oil phase and a rag layer formed between the phases are visible from the exterior of the desalter vessel;
    a heated jacket surrounding the desalter vessel; and
    at least one light source positioned adjacent to the desalter vessel, wherein the light source is directed through the substantially transparent portion and through the wash water phase, the crude oil phase, and a rag layer to aid in visualization and testing of the demulsification process.

2. The desalter simulator of claim 1 wherein the light source produces light in the visible light spectrum.

3. The desalter simulator of claim 1 wherein the light source produces light in the near IR light spectrum.

4. The desalter simulator of claim 1 wherein the light source produces light in the UV light spectrum.

5. The desalter simulator of claim 1 wherein the simulator processes between about 4 and about 20 liters of crude oil in an eight hour time period.

6. The desalter simulator of claim 1 wherein the oil vessel heats the crude oil contained therein to a temperature of at least 100° C.

7. The desalter simulator of claim 1 wherein the pump is a metering pump.

8. The desalter of claim 7 wherein said metering pump is a progressive cavity pump.

9. The desalter of claim 7 wherein said metering pump is a low shear metering pump.

10. The desalter simulator of claim 1 wherein the emulsion forming device is an electrically variable stirring device.

11. The desalter simulator of claim 1 wherein an electric grid is operatively associated with the desalter vessel so as to generate an electrostatic field in the desalter vessel.

12. The desalter of claim 11 wherein said electric grid is adjacent to said desalter vessel.

13. The desalter simulator of claim 1 wherein the desalter simulator contains multiple desalter vessels arranged in parallel channels, with each channel containing at least one chemical feed pump adding emulsion breaker chemicals to the crude oil and wash water in the channel, wherein the emulsion breaker chemicals added by a chemical feed pump in a first channel are different than the emulsion breaker chemicals added by a chemical feed pump in a second channel to facilitate comparisons of the effectiveness of the chemicals added in the first channel with the chemicals added in the second channel.

14. A method of testing emulsion breaker chemicals in a dynamic desalter simulator, the method comprising the steps of:
    drawing crude oil from a heated and pressurized oil vessel configured to hold a supply of crude oil;
    drawing wash water from a water vessel configured to hold a supply of wash water;
    adding at least one emulsion breaker chemical to the crude oil and/or wash water in the desalter simulator with at least one chemical feed pump;
    pumping the crude oil and wash water through the desalter simulator with a low shear metering pump;
    forming a crude oil-wash water emulsion with an emulsion forming device;
    resolving the crude oil-wash water emulsion in a heated desalter vessel such that the wash water and crude oil form distinct phases within the desalter vessel, with substantially desalted crude oil removed from an upper portion of the desalter vessel and substantially oil-free wash water removed from a bottom portion of the desalter vessel;
    passing light from a light source through a substantially transparent portion of the desalter vessel to visually monitor the presence of a rag layer formed at the interface between the crude oil phase and wash water phase using the light source; and
    adjusting parameters of the dynamic desalter simulator and monitoring the effect that the adjustment has upon the resolution of the emulsion, wherein the parameters adjusted are selected from the list of: rate of addition of emulsion breaker chemicals, type of emulsion breaker chemicals added, emulsion size, temperature of the desalter vessel, residence time of crude oil in the desalter vessel, and residence time of wash water in the desalter vessel.

15. The method of claim 14 wherein the light source produces light in the visible light spectrum.

16. The method of claim 14 wherein the light source produces light in the near IR light spectrum.

17. The method of claim 14 wherein the light source produces light in the UV light spectrum.

18. The method of claim 14 wherein the desalter simulator contains multiple desalter vessels arranged in parallel channels, with each channel containing at least one chemical feed pump, further comprising the steps of:

adding a first emulsion breaker chemical to a first channel with a first chemical feed pump;

adding a second emulsion breaker chemical to a second channel with a second chemical feed pump, wherein the first emulsion breaker chemical is different than the second emulsion breaker chemical; and comparing the rag layer in the desalter vessel in the first channel with the rag layer in the desalter vessel in the second channel.

19. The method of claim 14 further comprising the steps of:

continuously delivering the crude oil-wash water emulsion from the emulsion forming device into the desalter vessel through an input point of an emulsion input line; and selecting the height of the input point of the emulsion input line relative to the desalter vessel based on the type of desalter to be simulated.

20. A method as recited in claim 14 wherein said step of monitoring the effect that the adjustment has upon the resolution of the emulsion comprises observing the rag layer.

* * * * *